(12) United States Patent
White

(10) Patent No.: US 8,382,478 B2
(45) Date of Patent: Feb. 26, 2013

(54) METHOD AND MATERIAL TO FORM A CAST FROM GYPSUM

(76) Inventor: Dennis Joseph White, Plainsboro, NJ (US)

( * ) Notice: Subject to any disclaimer, the term of this patent is extended or adjusted under 35 U.S.C. 154(b) by 597 days.

(21) Appl. No.: 11/878,337

(22) Filed: Jul. 23, 2007

(65) Prior Publication Data

US 2008/0081317 A1 Apr. 3, 2008

Related U.S. Application Data

(60) Provisional application No. 60/851,360, filed on Sep. 28, 2006, provisional application No. 60/850,587, filed on Oct. 6, 2006.

(51) Int. Cl.
*A61C 11/00* (2006.01)
(52) U.S. Cl. .......................................... 433/213
(58) Field of Classification Search .................. 433/213
See application file for complete search history.

(56) References Cited

U.S. PATENT DOCUMENTS

| | | | |
|---|---|---|---|
| 3,620,778 A | 11/1971 | Morrell | |
| 3,650,031 A * | 3/1972 | Shilliday | 433/37 |
| 4,243,389 A * | 1/1981 | Eisner | 433/74 |
| 4,957,435 A * | 9/1990 | Jinoian et al. | 433/34 |
| 5,085,811 A * | 2/1992 | Hamer | 264/16 |
| 5,417,750 A | 5/1995 | Cohen et al. | |
| 5,466,152 A | 11/1995 | Walter | |
| 5,478,235 A | 12/1995 | Schuldt et al. | |
| 5,907,002 A | 5/1999 | Kamohara et al. | |
| 5,911,580 A | 6/1999 | Sharp et al. | |
| 6,045,359 A | 4/2000 | Tucker | |
| 6,099,305 A | 8/2000 | Browne et al. | |
| 6,149,426 A | 11/2000 | Singer et al. | |
| 6,152,731 A | 11/2000 | Jordan et al. | |
| 6,439,884 B1 | 8/2002 | Cronin | |
| 6,509,390 B2 | 1/2003 | Watanabe et al. | |
| 6,861,457 B2 | 3/2005 | Kamohara | |
| 7,021,929 B2 | 4/2006 | DiMarino et al. | |
| 7,210,932 B2 | 5/2007 | Honstein et al. | |
| 2003/0118970 A1* | 6/2003 | Rusin et al. | 433/213 |

OTHER PUBLICATIONS

U.S. Appl. No. 60/851,360, filed Sep. 28, 2006, D.J. White.
U.S. Appl. No. 60/850,587, filed Oct. 6, 2006, D.J. White.
http://artificialeyeclinic.com/fabricating_prosthesis.html.
LVI Visions Dec./Jan. 2005, p. 42.
DentalTown Magazine Jan. 2003 p. 22-28.
Laboratory Ad.
Contemporary Esthetics + Restorative Practice Sep. 2005 p. 56-57.
Dentistry Today Mar. 2007 p. 108-111.
Dental Collaborations Fall 2004 p. 18-20.
Inside Dentistry Oct. 2005.
Journal of the American Dental Association Jun. 2006 p. 794-800.
Phillips' Science of Dental Materials p. 219-272.
Testimonial Letter Jul. 3, 2007 1 pg.
Damon Adams, DDS, A Technno-Clinical Perspective Journal: Spectrum Dialogue, Oct. 2007 p. 68-72 vol. 6 No. 7 Palmeri Publishing, Schenectady, N.Y.
Erik K. Curtis, DDS, Made-to-Measure dentistry. Journal: AGD Impact., Apr. 2007 p. 40-44.

* cited by examiner

*Primary Examiner* — Sunil K Singh

(57) ABSTRACT

A method is disclosed for forming an accurate stone cast from an impression of a body region, used for the purpose of prosthetic fabrication, such as dental crowns and artificial eyes and hearing aids. The initial step with this unique method is to first acquire a suitable amount of dental stone catalyst. One type of a suitable stone catalyst is calcium sulfate dihydrate. The dental stone catalyst is engaged onto the internal surface of the impression. This catalyst, placed in the area between impression material and stone, will act to hasten the initial setting of wet, mixed dental stone that is in closest proximity to the impression. The result is a stratified set of the stone. Setting of the wet, mixed dental stone occurs first at the impression/stone interface. The mixed stone better resists distortion upon setting and the resultant set stone cast is more accurate.

6 Claims, No Drawings

METHOD AND MATERIAL TO FORM A CAST FROM GYPSUM

CROSS REFERENCE TO RELATED APPLICATIONS

This application is a continuation of U.S. patent application Ser. No. 60/851,360 filed Sep. 28, 2006, and U.S. patent application Ser. No. 60/850,587 filed Oct. 6, 2006.

FIELD OF INVENTION

This invention relates generally to making better fitting dental restorations and more specifically this invention relates to making accurate stone dental casts and models, which are used in the process of fabricating removable dental appliances and indirect dental restorations.

DESCRIPTION OF PRIOR ART

Stone dental casts need be very accurate replicas of the dentition. The cast, along with other exact measurements and guidelines supplied by the dentist, enables the laboratory to make dentures, partial dentures, orthodontic appliances, bleaching trays, and nightguards. Other special applications, such as oral snoring devices, obturators, and surgical stents, may also be prescribed by the dentist.

Once a cast is made, it can be sectioned so that segments can be removed. Segments representing individual teeth are referred to as dies. The dies are indexed in various ways to give an accurate and reliable placement of the removable die in and out of the model base. Some practitioners will refer to this dental cast with removable dies as a dental model. And they will refer to the one piece stone pour of the impression as a dental cast. However, many practitioners will still use the term "cast" and "model" interchangeably and do not distinguish between the two terms.

Dental models are used in the dental laboratory to create dental restorations which ultimately will be delivered to the dentist office. These restorations are then cemented into the patient's tooth with a cement, such as zinc phosphate cement. These cemented restorations are referred to as indirect restorations. Examples of indirect restorations would include inlays, onlays, veneers and crowns.

Conversely, direct restorations are those restorations that are buildup directly and incrementally into the patients tooth. Silver amalgams and composites are examples of direct dental restorations.

When initiating an indirect restoration for a patient, the dentist will first carve the tooth structure into a certain shape. This finished carved tooth shape is referred to as a prepped tooth, or simply, the preparation. After this step of tooth preparation is accomplished, impressions are taken to record the new altered dimensions, that is, a moldable material is impressed upon the tooth and allowed to set. Elastomeric materials are sometimes employed for this. Examples of elastomeric impression materials would include polyvinylsiloxane, polyether, and rubber base.

Another group of impression materials, called hydrocolloid, contain agar and water. Irreversible hydrocolloid is made by addition of water to a dry alginate formula. The resultant gel is in a moldable state for a given period of time. While it is in this moldable state it is impressed onto the mouth structures and held immobilized until it sets. Another agar containing impression material is reversible hydrocolloid. Reversible hydrocolloid is brought to a predetermined elevated temperature to form a gel. While the hydrocolloid is in this warmed gel state it is impressed to the oral structures. This reversible hydrocolloid is then cooled to final set in the mouth by using water cooled metal trays.

Collectively, all of the impression materials cure to the shape of the teeth and mouth. The impression material is removed from the mouth, capturing a negative image of the impressed area of the oral cavity.

In the lab, a wet mixture of stone is poured into the impression. Upon hardening, after an hour or so, the resultant dental cast is separated from the impression. This cast will be used as a mold in the process of fabricating removable appliances, such as dentures and the like.

The fabricated dentures are delivered to the patient by the dentist. Any irregularities in the fit of the appliance are located and adjusted by the dentist. A similar process takes place for all removable dental appliances.

Crowns are also delivered from the dental laboratory to the dentist office. These restorations are then modified and cemented for the patient by the practitioner. The crown must be adjusted with three parameters in mind. It must fit the tooth to which it is cemented to. It must be adjusted to the adjacent teeth to yield a certain tug feel with dental floss. And it must accommodate the opposing tooth cuspal relation so that the new crown is not high and does not strike the opposite tooth when the patient closes.

So the process of taking impressions avail the patient dentures and cast crowns. These products would be very challenging to make without an indirect technique.

And making stone casts from impressions is not exclusive to dentistry.

Similar to the process of dental appliance fabrication, is the process of artificial eye fabrication. The process of eye reconstruction is basically borrowed from the dental field. Dental impression materials are utilized directly or sometimes used with a modified viscosity to impress areas of the eye. The impressions are poured with gypsum products. In the most common technique, the sculpted pattern for the artificial eye is flasked for final process with the same techniques employed by a dental technician, who flasks a sculpted waxed denture, http://artificialeyeclinic.com/fabricating_prosthesis.html. And similar again to the above indirect processes, is the replication of the ear canal and related surrounding structures for the fabrication of hearing aids.

Impressions are taken for many specific prosthetic applications in form and function for other areas of the body.

OBJECTS AND ADVANTAGES

A tremendous problem exists with indirect dentistry. Dental appliances and indirect restorations seldom have a perfect fit. All mouth appliances, such as dentures, and all tooth restorations, such as crowns, need varying amounts of chair time to adjust. Distortions must be compensated for before finalizing the products.

In regard to acrylic appliances, professionals believe distortion may occur during the setting phase of the acrylic. Indeed, dentures do require multiple appointments to finalize. And usually, the final outcome is a slight disappointment. Dentures are usually tolerated by the wearer; dentures are seldom as tight fitting as the dentist would prefer.

Similar to the irregularities associated with dentures, acrylic nightguards also usually end up with a compromised outcome. It is very time consuming to troubleshoot an ill-fitting nightguard, in fact, many dentists have resorted to a soft inside liner attached to the hard outside acrylic shell. This laminate design is not so much for patient comfort, but for ease of delivery. The soft material is very moldable and therefore does not have to be a precise fit to the dentition. Its inherent conforming shape compensates for fabrication irregularities. However, the soft liner is not as durable and long lasting as all hard acrylic. Indirect restorations also require refinements. It is difficult to locate areas of distortions and most dentists allow up to an hour of office time to adjust and cement a crown.

The most difficult adjustment for the crown is the interproximal adjustment. This adjustment is tedious because it must be done slowly and incrementally, least too much is removed. If too much crown material is removed, an open contact is created. And if an open contact is inadvertently created by the dentist, then the crown must go back to the lab, and the patient must be scheduled for another appointment to complete the process. This scenario occurs occasionally to all dentists. It does not build confidence or self esteem. It may be confusing to the patient, since they know that the dentist took accurate dental impressions.

Having indicated that the most laborious crown and bridge adjustment for the dentist is the interproximal contact adjustment, the most important adjustment, in the inventor's opinion, is the actual fit of the crown to the prepared tooth structure. If there is any irregularity, the crown will not fully seat. Or, if the crown does fully seat, a slightly open margin may exist; that is, an open space existing between the crown and tooth. The crown may adapt well for most of the circumference around its margin to the tooth preparation, however, in one portion of the circle of the margin, there is lack of adaptation. The crown may fit the die well, but does not fit the tooth. An open margin would allow, over time, recurrent decay. It could also cause a floss catch or it could cause gingival irritation.

This internal fit of the crown to the tooth is best verified by a thick medium checker. Two examples would be FIT CHECKER, a product made by GC America, and DISCLOSING WAX, made by Kerr Manufacturing. The thick consistency of these products not only show where a point contact of interference may exist, preventing full seating, they also show how far off the internal surface areas are that are not touching.

Experience dictates that if there is distortion, the crown is too small and tight to the prepared tooth. It is always too small and never too large. If the interproximal contacts are off, the vast majority of time the contacts are too tight.

Much frustration exists. For example, one attached article from LVI VISIONS, illustrates an experience of ill-fitting restorations. Of note, is that the inquiring dentist is not contacting the dental school, the laboratory, or the manufacturers. Although there is technical support available from authoritative sources, no information exists anywhere that allows a dentist to make consistently accurate indirect restorations.

The attached article from DENTALTOWN MAGAZINE, shares a common experience; that the cast partial denture framework may fit the stone cast and not fit the mouth. The attached ad from a dental lab shows ill-fitting restorations could cost a dentist substantial income.

My own dental professor/preceptor from dental school sought out the very best students after they had graduated. She wanted these gifted students to do her own personal dentistry. She related to me that she was never satisfied with any restoration.

I share the above information to point out that a very real problem exists in dentistry. Experts attempt their best for answers, but these are never complete, and indeed, can be misleading. The expert dentist responds in the LVI VISIONS article that the problem, of ill-fitting crowns, lies with the impression technique.

In CONTEMPORARY ESTHETICS AND RESTORATIVE PRACTICE, the author suggests that hydrocolloid impression materials avail superior dimensional accuracy.

In DENTISTRY TODAY, the author implies rigid materials in metal trays are most accurate. He also indicates that quadrant trays allow damaging movement by the patient's cheek and tongue and this unwanted movement will cause distortion.

Another dentist shares, in INSIDE DENTISTRY, that impressions should be removed with a rapid pull. He also feels that the shrinkage of the impression material should be offset by an equal expansion of dental stone. He comments that addition silicone materials give the lowest shrinkage.

The fact that experts give varying reasons for the problems proves first of all that the problems really do exist. This reality of ill-fitting restorations is best summarized by Sharp, et al. in U.S. Pat. No. 5,911,580. In column 1, they describe the normal process of a dentist usually having to adjust an appliance. They write of the possibility that the final outcome may be that the appliance can not be adjusted adequately. The appliance sometimes needs to be remade.

Prior art shows that there have been many attempts to identify the cause of ill-fitting crowns. In U.S. Pat. Nos. 6,045,359, 5,478,235, and 7,021,929 inventors modify dental impression tray designs. They hope to achieve better bonding between the impression material and the tray. Although it is true, that a bond is needed to the tray, any severe defect such as tray separation would create a gross discrepancy in fit of final appliance. These separations are usually evident to the practitioner at the time of tray removal from the oral cavity. Impression tray design alone has never made a further refinement in the fit of our dental castings.

Inventors of prior art have attempted to create new impression materials to increase accuracy. In U.S. Pat. Nos. 6,861,457 and 5,907,002 Kamohara recognizes the inaccuracies associated with polyether impression material. He further isolates the problems of inaccuracy to impression tray removal. He feels that recovery from deformation applied during time to remove the impression causes dimensional instability.

He feels the solution for ill-fitting crowns is a more accurate impression material. With all of the impression materials on the market today, including the new ones introduced by Kamohara, there is very little improvement in the reliability of indirect dentistry.

Some inventors believe the inaccuracies occur after the impression is completed. They feel distortion occurs in the modeling process. This is the case with inventor Singer in U.S. Pat. No. 6,149,426. He states that inaccuracies occur with the master cast. His prior art confirms that the prosthetic must be fitted and corrected several times before it becomes accurate. He further feels that the problem, however, exists in the plastic trays used in the profession as well as subsequent modeling of the impression. His invention does not yield a better fitting crown.

Many inventors have come up with new designs for modeling. In U.S. Pat. Nos. 7,210,932, 6,439,884, 5,466,152, 6,099,305 and 4,957,435 inventors have shared efficient modeling devices. All of these systems would serve the profession well. However, they all share a common flaw. All of these inventors specify that the systems they have invented allows for a one pour of impression material and base. They all specifically state that the wet, mixed dental stone can be poured into the impression material and poured into the base, with the inversion of the impression so that the stones of material and base intermingle and set as a single unit. One pour is a common practice in laboratory technique. However, no inventor or researcher has ever discovered that inversion of poured impression material usually distorts the setting dental stone. The technique unknowingly causes a distortion. This concept is understandably elusive because the dies are still sharp with great detail from the impression. However, enough distortion occurs, so that the final product is flawed.

Some inventors attribute a smooth stone cast and easy separation of the set cast from the impression as indications of accuracy. This is the case in two U.S. Pat. Nos. 5,907,002 and 3,620,778. Present day dental casts are distorted due primarily to shrinkage. Any reference to easy separation of dental cast would have this inventor immediately equate to dental cast shrinkage. Most casts today exhibit distortion due to shrinkage.

In U.S. Pat. No. 5,417,750 Cohen and Musikant includes calcium sulfate in his alginate impression material. This is also true with inventors Watanabe and Kamohara in U.S. Pat. No. 6,509,390. Most alginate formulas rely on addition of calcium sulfate to alginate formulas to act as a catalyst and binder for set and strength of alginate. Calcium sulfate forms a cross link with the alginate material. These alginate formulas are all good performers as impression materials, however the ingredients of alginate have never acted to cause any type of catalyst effect on the wet, mixed stone poured into and against it. Stone dental casts made from alginate exhibit just as great a distortion as with other dental impression materials.

Five percent potassium sulfate solution is available from American Dental Supply, Inc. This product is available to help condition hydrocolloid impressions. It may help to provide a smoother cast surface, but does not provide a more accurate cast.

In June 2006 issue of the JOURNAL OF THE AMERICAN DENTAL ASSOCIATION, Carl J. Drago, D.D.S. stated that the long term success of crowns and fixed partial dentures on natural teeth and implants depends on several variables: accuracy of fit between castings and abutments and teeth, impression materials and techniques, manipulation of dental stone, and casting and finishing processes.

The only problem with all of the above is that, heretofore, no one has come up with the correct combination to produce accurate castings.

PHILLIPS' SCIENCE OF DENTAL MATERIALS, edited by Kenneth J. Anusavice, PhD, DMD., states that if a partially set impression material is seated, it will be compressed elastically. Once the material has set completely, and the tray removed, then there will be a certain amount of spring back. This would cause the impression to produce smaller dies. The crowns made from such distorted dies would be tight to the tooth. Although this theory offers some limited insight, the persistent problems still cause frustration.

One dentist feels the error occurs when the technician fits the crown to the model.

He feels that the technician inadvertently removes a small amount of stone when the prosthetic crown is tried on and off repeatedly from the die. This wearing away produces a crown that is too wide.

Another dentist shared with this inventor that she feels the error exists in her impression; that the impression distorts in some way. She also feels that in some cases, the fault lies with the technician, so she'll change dental labs.

As one experienced dentist once related to me: he simply gave up. He gave up trying to troubleshoot the error.

The experienced dentists usually do not share comment on outcome of prosthetic dentistry. Because of this, dental technicians at the laboratories feel that the experienced dentist has certain skills and techniques that he has acquired over his career to enable him to make perfect crowns. Perhaps the more experienced dentist is more efficient at adjusting crowns, but his crowns fit no better than anyone else's. The inexperienced dentists are always trying to troubleshoot the problem, yet, in fact, experienced dentists learn that no solution exists.

There are so many steps in the dentist office, along with an equally complex arrangement in the laboratory, that dentists believe the solution for ill-fitting prosthetics, can never be achieved.

The textbook of PHILLIPS' SCIENCE OF DENTAL MATERIALS states the hydrocolloid may often contain borax additive, which strengthens the gel. Borax is thought to be a gypsum setting retarder. Potassium sulfate, which is an accelerator, is added to hydrocolloid to counter the effect of borax. Potassium sulfate is also believed to be a dental stone catalyst.

However, the potency of potassium sulfate as a dental stone catalyst is not clear to this inventor. Many impression materials have incorporated potassium sulfate, but none have produced accurate casts. Because the correlation between a stratified stone set and cast accuracy is unknown, the effective amount and combination of dihydrate ingredients remains undiscovered. A corrected formulation would allow significantly more accurate dental casts.

Still further, this inventor has used potassium sulfate solution for many years with different hydrocolloids, reversible and irreversible. And this inventor has found no appreciably faster times for setting of gypsum. Also, even adding the potassium sulfate solution directly to wet mixed gypsum, this inventor could still not verify any difference in setting time as compared to a control mix. And not only setting time, but also, no change in accuracy between potassium sulfate stone mixes versus control mixes could be verified, by this inventor. There are no studies, known to this inventor, verifying more accurate castings using potassium sulfate conditioned impressions.

The PHILLIPS' SCIENCE OF DENTAL MATERIALS textbook goes on to suggest the incorporation of an accelerator additive, such as potassium titanium fluoride, into dental impression material. It suggests that this be added to the hydrocolloid directly to accelerate set time of dental stone. It is important to emphasize the reason accelerators are suggested by researchers, is that ingredients such as borax will retard the setting of stone. If the stone does set satisfactorily, impression and stone manufactures feel materials are compatible. They do not go further to produce a unique product that will definitively set stone, faster than a normal set, closest to the impression material/stone interface. This inventor has used an alginate material containing potassium titanium fluoride made by Zhermack for several hundred impressions. This material does not produce accurate stone casts from the first pour.

Besides the Zhermack product, for thirty years, this inventor has used JELTRATE, an irreversible hydrocolloid made by Dentsply. It also contains potassium titanium fluoride. Casts rendered from this product are no more accurate than other impression materials. This inventor recognizes the literature has made suggestions to include catalysts to dental impression materials. Indeed, manufactures have included stone catalysts. Without the catalysts, apparently, either the stone did not set or the stone setting took a very long time. However, manufacturers have never formulated impressions to cause the stone to set faster than the normal set time. No formula causes a stratified set of stone, that is, causing stone to set first, closest to the impression. Further, no manufacturer had this goal. It is not known that the actual effect of a suitable catalyst goes far beyond simply setting of stone, it produces new dimensions of accuracy to the cast.

Although catalysts are included in many impression materials, still, some present day manufacturers do not add stone catalysts at all. The largest reversible hydrocolloid manufacturer offers to the profession, a half dozen impression materials, but only one of these products contain stone accelerator and it happens to be their least selling brand. Die spacer may be applied to the die to compensate for shrinkage inherent to the system of modeling. However, stone die distortion occurs in random places and also to varying degrees. The deformation is unpredictable. So, if there is distortion, no amount of die spacer will compensate.

Also, die spacer can not be extended the entire length of the die. Spacer is not used to cover the margin. Die spacer on the margin of the die will cause an open margin of the crown preventing close adaptation to the tooth structure.

This inventor does not use die spacer. Applying die spacer is an unnecessary step in view of the accuracy produced from this invention.

Removable appliances are also problematic. When the fit of new dentures is verified by the dentist, the buccal flanges tend to be tight along the outside alveolar ridge. The palatal area is usually distorted, so that space may exist between the palate and the internal surface of the denture. Removable appliances are also adjusted using a thick film medium. Dentists, using present day technology, trudge through the process of delivering the less than perfect indirect restorations, believing this is as good as it gets. They feel that the errors we see are a reflection of the limitations of the accuracies of all the systems involved. Professionals, familiar to the art, believe variables occur cumulatively with impression distortion, setting of dental stone, waxing techniques, investing and casting, and firing porcelain.

Appreciatively, after time is spent adjusting present day crowns, some crowns will fit very near perfect. However, some crowns can never be adjusted well enough for clinical acceptance. Crowns that are distorted beyond clinical acceptance become remakes. Remakes are a disappointment to dentist as well as the patient. One dental laboratory owner admits his remake rate is 11%.

Realistically, most crown fit accuracy probably falls into a nebulous area. The crown is adjusted as well as possible, but the dentist is forced to accept slight imperfection. This is necessary. Taking another impression does not guarantee a better result.

Distortion associated with indirect dentistry is the primary reason for growth of the use of CAD/CAM in dentistry. In U.S. Pat. No. 6,152,731 Jordan et al. describe how dentistry is moving toward digital images. Although digital images are an improvement in efficiency, cost is certainly a factor. And as far as overall accuracy, the concepts of the enclosed disclosure produce results that rival those of the CAD/CAM systems.

In the area of prosthetic eye fabrication, delivery and patient tolerance is also a problem. Due to distortions of shape from processing, eye wearers must return for adjustments to the prosthesis, just as denture patients return to the dentist.

Hearing aids made from impressions are no different. Inaccuracies are a problem. A certain percentage of dentures, artificial eyes, and hearing aids are returned to the laboratories for remakes.

There are many professions that have borrowed from the impression techniques of dentistry. Along with this borrowed technology came the problems of distortions; distortions that were never fully addressed in dentistry. No inventor or researcher has ever isolated the cause of distortion associated with indirect dentistry.

The advantage of this disclosure is to avail accurate indirect dental restorations, hearing aids, and artificial eyes.

SUMMARY OF THE INVENTION

A dental impression is procured in the usual manner, a manner familiar to the dentist. This inventor has found no specific correlation to any specific type of impression material, or to any specific style of tray design, that effects final outcome.

This set impression is placed aside for use in the dental lab.

Acquisition of powdered calcium sulfate dihydrate, or adequate substitute, is the initial step. This inventor produced calcium sulfate dihydrate by mixing dental stone with water and allowing full set. The resultant set dihydrate stone is then ground into a powder with a fine acrylic adjusting bur.

Calcium sulfate dihydrate powder is shaken lightly onto the internal surface of the impression. This powder is burnished with a suitably stiff artist brush onto the impression surface. Excess loose powdered calcium sulfate dihydrate is blown away, leaving a light dusting held in intimate contact to the surface of the impression.

Last, the dental impression is poured with wet, mixed dental stone.

DETAILS OF THE PREFERRED EMBODIMENT

Preferably, the impression filled with wet mixed dental stone is maintained in an upright position until the dental stone completely sets. The inventor has found that is many cases, inversion of the impression will allow gravity to have a detrimental effect on the accuracy of the set stone cast.

It may also be desirable to use a fine tip syringe, such as a MONOJECT 412, manufactured by Tyco International. Using such a tip provides for a direct deposit of wet mixed dental stone directly into the tooth prep of the dental impression. This more precise initial deposit of the wet stone will not be as likely to disturb the location of calcium sulfate dihydrate. That is, wet mixed stone first vibrated into the impression along its outside border, the usual accepted technique, could possibly wash stone catalyst off the sides of the impression and have the catalyst inadvertently contact the wet unset stone away from the impression surface.

It is also better to use a disposable bowl and very clean mixing spatula for mixing each dental stone batch. Any errant set stone particle from a previous stone mix would detrimentally serve as a catalyst to start the setting of wet dental stone at a site away from the impression surface. That is, any catalyst suspended within the wet stone mix will compete with the desired setting of wet stone juxtaposed to the surface of the impression.

CONCLUSIONS, RAMIFICATIONS AND SCOPE OF INVENTION

Implementation of this discovered technique enables dental impressions to yield more accurate casts than present day technology.

This distinctive invention advances dental restorations beyond present art and this invention improves the overall standard of care.

Accuracy, to this level, has never been appreciated in dentistry. This disclosed technique will add normalcy and stability to a process that, heretofore, is far from predictable. This new technique is the answer to what may be the last major challenge in our profession. To be able to reduce procedural time significantly is not to be understated. This technique will not only cut delivery time for the dentist in half, it produces a better product. Patients will enjoy restorations that will feel better and last longer.

Benefiting from new, improved accuracy, we can now further our studies and discoveries. For instance, numerous studies have been published comparing accuracy of various techniques and materials in use today. One notable experiment was to compare the accuracy of various impression materials after immersion into cold sterilizing solutions. Many of these studies were done in the early 1990s. It was determined that polyether was the very likely to distort from gluteraldehyde sterilization.

Other studies determine how long an impression is dimensionally stable in the laboratory before pouring. I have seen studies comparing die stone dimensional accuracy in use with different impression materials. Other studies examine powder/water ratios of die stone, effect of humidity on both impression materials and die stones, and effects of vacuum. Countless other studies for accuracy in dentistry are ongoing.

The inventor feels that data from studies, do not consider the effects described at length in this application. In short, much of the data may not be accurate.

For another example, there is in dentistry, a timeless misconception that most alginate impression materials are well suited for removable appliances, but are not accurate enough for crown and bridge. This concept is widely held and even supported in the PHILLIPS' SCIENCE OF DENTAL MATERIALS textbook. It is held that alginate impressions have a course surface finish and that, dimensionally, the material is inaccurate.

This misconception of alginate accuracy stems from observations of inaccuracies occurring largely as a result of the stone distortion; the inaccuracy is only slightly from the alginate impression material. Attached is a photo, FIG. 1, of a stone die made from an alginate impression for a single unit crown. The sharpness and detail of this die is no different to the eye than for dies made from conventional elastomeric impression materials, as in the example in FIG. 2. This second photo is of a stone die made from a polyether impression material. There are no clinical differences between the final restorations made from the two different impression materials. Many of our dental materials, at some point, are misrepresented, causing much frustration in the profession. To utilize this invented technique, acquisition of powdered dental stone is achieved and this can be accomplished by most technicians. The powdered catalyst can be stored for later use. A small portion of powdered catalyst can serve for many impression pours. The dental stone manufacturers could supplement their current products with a separate inclusion of dental stone catalyst. This packaging from the manufacturer would be more efficient, saving the dentist or technician the time and effort of producing their own powdered catalyst. This would also allow for a more uniform product by grinding to a finer particle size.

Hopefully, a generic catalyst would be produced that would not be stone type specific. This catalyst could be made available for use that would be compatible with all dental stones. This inventor has not yet studied all the various combinations of catalysts used with different brand and type dental stones.

In addition to the powdered form of catalyst described above, dental stone catalyst could be made available in a liquid slurry form. Such a liquid product would allow for a dipping of the impression. The liquid will evaporate, only to leave a thin precipitate film coating on the impression material to act as a dental stone catalyst.

Another embodiment for this discovery would be to simply pour a second cast from the original impression. The original cast can be discarded. The purpose of this first stone cast would be to leave a layer onto the impression surface of calcium phosphate dihydrate to serve as catalyst. Unobvious to even those expert in the art, the second cast retrieved from the impression will be dimensionally different from the first cast; it will be more accurate cast than the first cast.

This is a very significant point and is best summarized in the attached article from DENTAL COLLABORATIONS. The author points out that the second solid model is useful for adjusting after the prosthesis is fabricated. It is not inherently obvious to use the second model for fabrication and to actually discard the first retrieved cast.

Similarly, it is believed in the art that modeling a base to accommodate removable dies may introduce some inaccuracies. Second pour casts are sometimes made to provide a one piece cast to make final interproximal crown adjustment. This second pour of the impression acts as a safety net to correct inaccuracies that may occur due to modeling. Agreeably, this practice will provide interproximal accuracy. It provides accuracy because it is a second pour, the first pour providing a catalyst for a stratified set of the subsequent poured casts. The actual reason for perfect contacts is not from inaccuracies from structuring a pined a model; this would be negligible. No one knows that the real reason for perfect contacts is that the second model has different dimensions. Again, this is not intuitive; both models appear sharp in detail.

The second pour, however, does not provide internal accuracy for the crown, which is made on the original poured stone cast die. The resultant crown will have accurate interproximal contacts, but the internal fit of the crown will be tight to the tooth. Interestingly, many labs believe also, that second pours will not aid accuracy to the die itself. In fact, the textbook, PHILLIPS' SCIENCE OF DENTAL MATERIALS, states that several pours, of stone dies can be made from polyether and addition silicone impressions, due to dimensional stability of the impression material. The textbook notes however, that each subsequent die will be less accurate than the very first die.

Another instance when a second pour may be utilized is with acrylic appliances. The appliance is made from the original cast, yet may sometimes be finished to the second pour. This technique would not be as efficient as actually fabricating directly to the second cast. The disadvantage of adapting the appliance to a second pour cast is that this adjustment is time consuming. It would be a very tedious process and this would become an almost reverse carving technique, meaning, if a technician had enough time, he could carve the end result starting from a solid block of acrylic. Even so, the end result would probably also be a compromise to a perfect fit.

Although the second pour technique works for most impression material types, the second pour technique is especially compatible with hydrocolloid impression material. The wet, mixed stone is more likely to be absorbed within the hydrocolloid, due the water content of both stone and impression material. Set dihydrate stone is imbedded into the hydrocolloid surface, ready to seed the set of the subsequent pour.

More efficiently though, hydrocolloid having a stone catalyst self-containing would circumvent the second step of pouring another cast. The double pour technique has a distinct disadvantage. Imperfections may be present within the impression, such as bubble porosity, near the margin. Separating the set stone of the first pour will tear the unsupported margin at a critical area of the hydrocolloid impression, rendering it useless for the second pour.

Therefore, one embodiment would be irreversible hydrocolloid impression material manufactured with the stone catalyst contained within the material. For example, dry calcium phosphate dihydrate could be mixed with the dry alginate powder.

Also, stone slurry could be included within the water portion of irreversible hydrocolloid. In like fashion, a stone slurry could also be added into reversible hydrocolloid.

Elastomeric dental impressions could also be manufactured with a dental stone catalyst included within. This would eliminate the step of burnishing the catalyst onto the impression.

Impression materials could be modified to set with a texture surface to better hold the catalyst onto its surface. Catalyst powder may more readily adhere to a course impression surface. Conversely, the catalyst may be harder to attach to a glossy impression surface. Impression materials could be modified to accept an electrical conduction to better attract an ionized catalyst. A charged attraction between impression material and catalyst would create more certainty in holding the catalyst in place. The catalyst would be less likely to drift into the wet mixed dental stone. And the stone itself may be charged for a better attraction to hold against the impression/catalyst interface.

Setting stone catalyst could be formulated to be dispersed onto the oral structure directly. If it were attached to the teeth, the catalyst could be picked up by the impression.

Attaching this way to the uncured impression material may have a benefit of a deeper, more tenacious bond between impression material and stone catalyst.

The end result of this discovery is that all indirect restorations fit with 90% more accurate. Enclosed is a letter of substantiation from the only other dentist knowledgeable of this technique.

FIG. 3 confirms accuracy of a crown, fabricated from the new disclosed technique, against tooth structure. DISCLOSING WAX is thinned out evenly over the entire internal surface of the molar crown. This reflects a very close adaptation of the crown to the tooth structure.

Heretofore, this inventor would need to adjust the internal fit of the crown. Poor adaptation would be the normal outcome and is exemplified in FIG. 4. Perforations of DISCLOSING WAX are made by point contacts of the crown to the tooth. These revealed points of contact would need to be relieved. The process is repeated many times until an adequate fit is achieved.

Partly because of the limitations of present day technology of pouring casts, we are now turning toward a digital world of CAD/CAM indirect restorations. These machines are very expensive, and still have limitations. They can not make a custom shaded crown, which may be necessary to match a single maxillary anterior tooth. This is a serious drawback in today's esthetic conscious world. And the CAD/CAM machines can not make dentures, partials, nightguard, or bleaching trays.

The concept of perfect fitting restorations is incomprehensible to expert professionals. Finding the necessary techniques to accomplish this would be equally obscure. Please consider that there are over one hundred thousand dentists in this the United States alone, who are fabricating over twenty million crowns a year.

This invention has remained undiscovered due to: 1. the complexities of indirect dentistry, 2. stone setting accelerators have already been used in impression materials, with no added benefit to cast accuracy 3. second pours, although not used for fabrication, are already performed and are not new to the profession, and 4. lastly, the end result of a consistent near perfect restoration has, heretofore, never been achieved in dentistry.

This unique disclosure is long overdue. The profession has accepted status quo level of accuracy in dentistry for a very long time.

I claim:

1. An improved method for producing a stone dental cast comprising the steps of:
   a. placing thin layer of dental stone setting catalyst, onto the internal surface of an elastomeric dental impression;
   b. pouring a wet, mixed dental stone into said elastomeric dental impression and onto said catalyst,
      whereby the dental stone juxtaposed to said catalyst sets faster, and further whereby, an accurate gypsum cast is formed by a stratified set, thereby, producing accurate restoration or prosthesis.

2. A method according to claim 1, wherein said dental impression is maintained in an upright position until said wet, mixed dental stone sets.

3. A method according to claim 1, wherein said dental impression comprises texture.

4. A method according to claim 1, wherein said dental impression is electrically charged.

5. A method according to claim 1, wherein said dental stone setting catalyst comprises dental stone remnant attached to said internal surface, from a previous stone pour.

6. A method according to claim 1, wherein said dental stone setting catalyst is a thin veneer of wet mixed dental stone, that sets to form a thin catalyst layer.

\* \* \* \* \*